United States Patent [19]
Crivello

[11] Patent Number: 5,073,643
[45] Date of Patent: Dec. 17, 1991

[54] HIGH YIELD SYNTHESIS OF HYDROXYL-CONTAINING CATIONIC PHOTOINITIATORS

[75] Inventor: James V. Crivello, Clifton Park, N.Y.

[73] Assignee: Polyset Corporation, Round Lake, N.Y.

[21] Appl. No.: 575,276

[22] Filed: Aug. 30, 1990

[51] Int. Cl.$^5$ .......................... C07F 5/02; C07F 9/90; C07F 9/92; C07F 9/00

[52] U.S. Cl. ................................. 556/64; 427/54.1; 522/15; 522/25; 568/6; 568/16; 568/17; 568/28; 570/123; 570/130

[58] Field of Search .............. 556/7, 41, 64; 522/15, 522/25; 568/6, 8, 16, 17, 18, 24, 28; 570/101, 123, 130; 427/54.1

[56] References Cited

U.S. PATENT DOCUMENTS

| | | | |
|---|---|---|---|
| 4,090,936 | 5/1978 | Barton | 204/159.18 |
| 4,329,300 | 5/1982 | Crivello et al. | 556/41 X |
| 4,450,360 | 5/1984 | Crivello et al. | 556/41 X |
| 4,683,317 | 7/1987 | Crivello | 556/64 |
| 4,882,201 | 11/1989 | Crivello | 427/54.1 |

OTHER PUBLICATIONS

Crivello, Conlon, Olson & Webb; "The Effects of Polyols As Chain Transfer Agents and Flexibilizers in Photo initiated Cationic Polymerization"; J. of Rad. Curing; Oct. '86, pp. 3–5.

*Primary Examiner*—Arthur C. Prescott
*Attorney, Agent, or Firm*—Schmeiser, Morelle & Watts

[57] ABSTRACT

Synthesis use of a new class of diaryliodonium salt photo and thermal polymerization initiators in which the aryl groups are substituted with alkoxy group bearing hydroxy groups. Good to excellent yields are obtained of diaryliodonium salts in which the aryl groups are substituted with long chain alkoxy groups, which alkoxy groups also possess at least one hydroxyl moiety attached at the 2-position of an alkoxy group. The resultant salts have enhanced solubility when compared with their lower molecular weight counterparts. The hydroxyl groups serve as chain transfer agents; and, in cross linking UV-induced cationic polymerizations, the hydroxyl groups effect marked accelertion on polymerization rates. The salts also have excellent compatability with nonpolar monomers such as epoxidized oil and poly(1,2-butadience oxide) and provide further benefits when they are used along with copper cocatalysts in thermally curable polymer systems. In the latter form of cases, the secondary hydroxyl group serves as a reducing agent for the copper (II) complex.

6 Claims, No Drawings

HIGH YIELD SYNTHESIS OF HYDROXYL-CONTAINING CATIONIC PHOTOINITIATORS

RELATED APPLICATIONS

This application relates to U.S. Ser. No. 558,627, filed on July 27, 1990 and entitled: PREPARATION OF DIARYLIODONIUM SALT PHOTOINITIATORS HAVING LONG CHAIN ESTER GROUPS CONCATENATED WITH ARYL GROUPS, by James V. Crivello, the instant inventor. The earlier application is incorporated herein by referece.

BACKGROUND OF THE INVENTION

1. Field Of The Invention

This invention relates generally to photoinitiators used in cationic polymerization, and specifically to the synthesis and use of a new class of diaryliodonium salt photo and thermal initiators with aryl-substituted alkoxy groups bearing therewith hydroxy groups.

2. Discussion Of The Art

In the past several years, photoinitiated cationic polymerization has received considerable attention as a rapid, energy efficient and pollution-free method for the cure of epoxy monomers. It has been discovered that certain onium salts, namely diaryliodonium (I) and triarylsulfonium (II) salts, rapidly and efficiently photoinitiate the polymerization of practically all types of cationically polymerizable monomers:

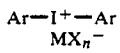
(I)

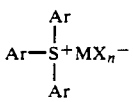
(II)

Where $MX_n^- = BF_4^-, PF_6^-, AsF_6^-, SbF_6^-$, etc.

Because the above classes of compounds could be synthesized with relative ease, together with high quantum yields of photolysis and exceptional thermal stability in the presence of monomers, they became the first truly practical photoinitiators for cationic polymerization. These facts and others are pointed out clearly and succinctly in a paper prepared by the instant inventor and colleagues Conlon, Olson and Webb, entitled: "The Effects Of Polyols As Chain Transfer Agents And Flexiblizers In Photoinitiated Cationic Polymerization", Journal of Radiation Curing, 3-9, October 1986. Within the industry, diaryliodonium and triarylsulfonium salts continue to be the principal photoinitiators for cationic ultraviolet (UV) curing. Diaryliodonium salts having the structure shown in (I) have been described in the patent literature as efficient photoinitiators for cationic polymerization, notably in U.S. Pat. No. 4,683,317 issued in 1987 to the instant inventor, J. Crivello, and colleague J.L. Lee. Therein, the subject salts result from the condensation of aryliodosotosylates and aryl ketones. The salts are used as photoinitiators to effect deep section UV cures in (deep section) photopolymerizable organic materials used for the encapsulation of electronic components.

As pointed out in the Journal of Radiation Curing article, there are two major advantages to UV curing using photoinitiated cationic polymerization. The curing systems require no blanketing by inert gas because they display no inhibition by oxygen; and, many of the photoinitiated cationic polymerizations undergo substantial post cure after initial irradition. The postcuring property, which can be accelerated by heating, may readily suffice in applications where an immediate cure of the coating, having been inadequate, is not absolutely essential.

Notwithstanding, the existing postcure effect, it has been determined that when multifunctional epoxy monomers are UV cured, using photoinitiated cationic polymerization, the cure rate passes through a maximum, and then falls off rapidly. This factor is revealed also in the aforementioned article. The same effect is observed when multifunctional vinyl monomers are polymerized using free radical photoinitiators. In such network forming systems, polymerization proceeds rapidly until gelation occurs. At this point, polymerization markedly slows, but can still occur as monomers diffuse to the fixed propagating sites within the swollen gel. As the gelation temperature of the network reaches the region of the temperature at which UV curing is taking place, vitrification sets in, monomer diffusion is impeded, and polymerization virtually ceases. Delaying the onset of gelation so that it closely approaches the point of vitrification assures an overall high polymerization rate, thus obviating existence of sizable unreacted (but polymerizable) groups within the UV-cured coating. The instant inventor and his colleagues determined that, in photoinitiated cationic epoxy systems, such results can be achieved with the use of chain transfer agents, specifically hydroxyl-containing compounds such as water and alcohols.

In U.S. Pat. No. 4,090,936, issued to Barton in May 1978 and entitled "PHOTO HARDENABLE COMPOSITIONS", a class of diaryliodonium salts is disclosed in which aryl groups have been defined as composed of aromatic groups or arylalkyl groups containing from 6 up to, but not more than, 20 carbon atoms. Salts having more carbon atoms were specifically excluded from this disclosure. In another patent recently issued to the instant inventor, U.S. Pat. No. 4,882,201, diaryliodonium salts possessing alkoxy groups of differing lengths were described as non-toxic photoinitiators; however, no disclosure is made therein of similar diaryliodonium salts containing other functional groups, particularly with long carbon chains. Most notably, there is a complete paucity in either the patent or chemical literature of descriptions or disclosures of diaryliodonium salts possessing hydroxyl-containing alkoxy groups attached to the aryl moieties; such salts have now been made with high yields and are hereinafter described. Likewise, the aforementioned related application teaches the method for obtaining significant (quantitative) yields of soluble diaryliodonium salts having alkoxy groups of more than twenty carbon atoms attached to an iodine atom.

SUMMARY OF THE INVENTION

Diaryliodonium salts in which the aryl groups bonded to iodine contain hydroxyl-substituted alkoxy groups are not known, not having been previously reported in the art.

Quite unexpectedly, the instant inventor has discovered that it is possible to prepare in good to excellent yield, diaryliodonium salts in which the aryl groups are substituted with long chain alkoxy groups which also possess hydroxyl moieties attached at the 2-position of the alkoxy group. Incorporation of these long chain hydroxyalkoxy groups into the aryl groups confers enhanced solubility to these salts compared with their lower molecular weight counterparts, notably the counterparts in which aryl groups, composed of aromatic groups or arylalkyl groups, attached to the positive iodine atom contain 20 or less carbon atoms.

The hydroxyl groups that are characteristic of the instant invention serve as chain transfer agents. In cross-linking UV-induced cationic polymerizations, it has been shown that such hydroxyl groups have a marked acceleration effect on the polymerization rates. On polymerization, the initiator residues become bonded to the matrix of the polymerizing resin, resulting in a decrease in the number of fragments of the initiator which can volitalize or leach out of the polymer film. This factor is of considerable importance for electronic applications in which the photoinitiator is used, since it is known that photoinitiator residues, having ionic character, may degrade electronic performance by interfering with hole/electron transport mechanisms.

An additional benefit arises when the instant iodonium salts are used along with copper cocatalysts in thermally curable systems. In such cases, the secondary hydroxyl group serves as a reducing agent for the copper (II) complex.

The photoinitiators of the invention are very reactive and, because of their high molecular weight and hydrocarbon-like character, are probably non-toxic (U.S. Pat. No. 4,882,201, ibid.).

Additional to their excellent solubility in most organic solvents, the new initiators have been found to possess excellent compatability with even such nonpolar monomers as epoxidized oils and poly(1,2-butadiene oxide).

DETAILED DESCRIPTION OF THE INVENTION

A general scheme for the synthesis of the diaryliodium salts of this invention is as follows:

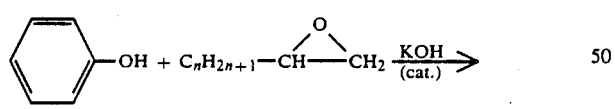

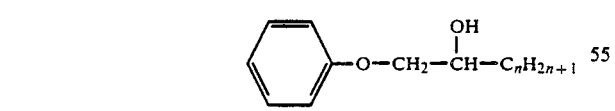

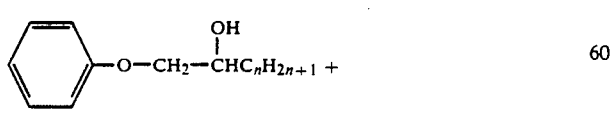

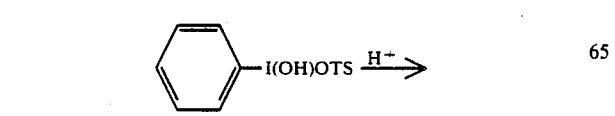

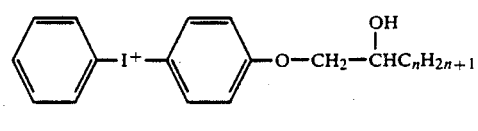

TsO$^-$

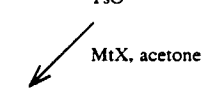

MtX, acetone

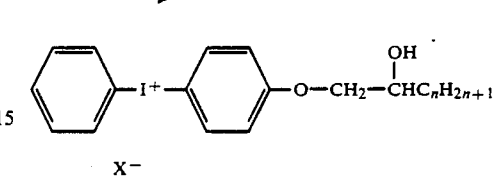

X$^-$

The above is a general synthesis which can be expanded to cover a large family of such photoinitiators. In this scheme, the values of n are integers from 0 to 25. X$^-$ in the above general formula includes those complex metal halide anions such as BF$_4^-$, PF$_6^-$, AsF$_6^-$, SbF$_6^-$, as well as anions of strong protonic acids such as ClO$_4^-$, CF$_3$SO$_3^-$, FSO$_3^-$, and CH$_3$SO$_3^-$ and C$_4$F$_9$SO$_3^-$. Among the many examples of such compounds are those shown below.

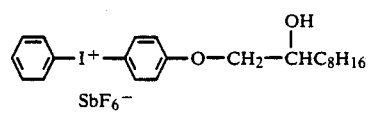

SbF$_6^-$

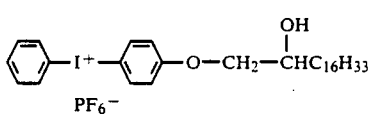

PF$_6^-$

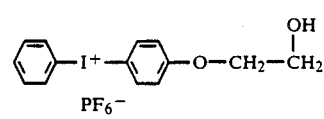

PF$_6^-$

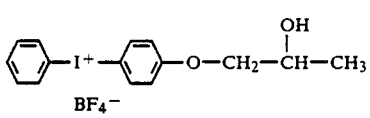

BF$_4^-$

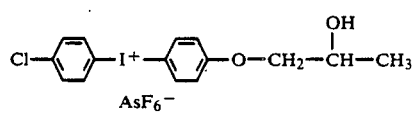

AsF$_6^-$

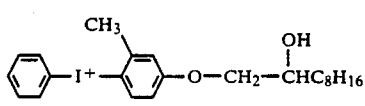

SbF$_6^-$

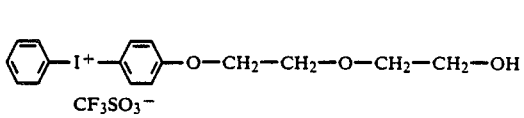

CF$_3$SO$_3^-$

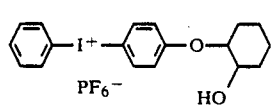

PF$_6^-$

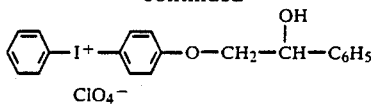

Thus, at least one of the aryl groups attached to the positively charged iodine atom bears moieties containing hydroxyl groups.

The initiators described in this disclosure may be used to carry out the photoinitiated polymerization of such cationically polymerizable monomers as mono, di and polyfunctional epoxides such as bisphenol-A diglycidyl ether, butanediol diglycidyl ether, 3,4-epoxycyclohexyl-3',4'-epoxycyclohexane carboxylate, phenol novolac epoxides, poly(1,2-butadiene oxide), epoxidized soybean oil, epoxidized linseed oil: vinyl ethers, such as diethyleneglycol divinyl ether, triethyleneglycol divinyl ether, dicyclohexanedioldivinyl ether, 1,4-butanediol divinyl ether; vinyl hydrocarbon monomers including styrene, c-methyl styrene, divinyl benzene, 1,3-diisopropenylbenzene, N-vinyl carbazole, and acenaphthalene. Heterocyclic monomers such as oxetane, trioxane, 1,3-dioxolane, and tetrahydrofuran can also be polymerized using these photoinitiators. The most useful but not exclusive applications of these photoinitiators are in formulations intended for use as UV curable coatings, adhesives and sealants. The photoinitiators can also be used for photoimaging purposes as in the fabrication of photoresists for electrical and electronic applications.

In addition, the same diaryliodonium salts are useful in combination with copper cocatalysts or free radical initiators as thermal initiators for the above cited monomers and polymers. These initiator/coinitiator combinations are useful in a wide variety of applications including molding, pulltrusion, composites, encapsulants, adhesives and foams.

Experimental
PREPARATION OF
[HYDROXY(TOSYLOXY)IODO]BENZENE
(MW = 394)

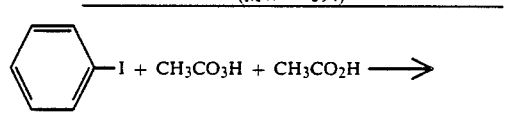

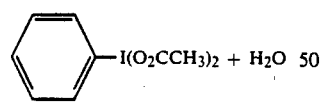

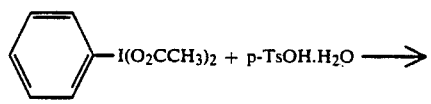

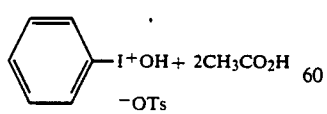

Placed in a 1L three necked flask fitted with an addition funnel, condenser, thermometer and paddle stirrer were 208g (1.0 mol, 98%) iodobenzene. To the iodobenzene were added, dropwise with stirring, 520g (2.4 mol) 35% peracetic acid. The temperature was maintained between 40 and 45° C. during the addition using a water bath. After addition was complete, the Yellow solution was maintained at 40° C. for one hour. Within 20 minutes a precipitate of iodosobenzene diacetate began to form and the solution became quite thick. Maintaining the reaction mixture at 40° C., there were added 298g (1.57 mol) p-toluenesulfonic acid in portions. As reaction proceeded, the solution became perceptively more fluid, then once again thixotropic as the product, [hydroxy(tosyloxy)iodo] benzene precipitated. The reaction temperature was maintained at 40° C. for two hours after addition had been completed. The product was isolated by suction filtration, washed with water and air dried. There were obtained 217.3g product. Yields ranged up to 97% theory.

EXAMPLE 1

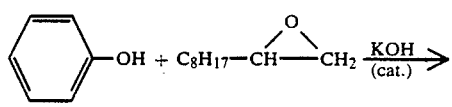

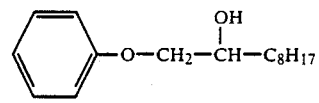

To a 100 mL round bottomed flask fitted with a magnetic stirrer, thermometer, and reflux condenser, there were added 31.2 g (0.2 mol) 1,2-epoxydecane, 20g (0.21 mol) phenol and 0.5g KOH as a catalyst. The reaction flask was slowly stirred and heated over the course of one hour to 170° C. After maintaining the reaction flask at this temperature for an additional hour, the reaction mixture was cooled and transferred to a separatory funnel, diluted with ether and extracted with aqueous KOH. The ether was removed on a rotary evaporator leaving a pale yellow oil which, on cooling, rapidly crystallized. There were obtained 50.6g (a quantitative yield) of the desired 1-phenoxy-2-hydroxydecane.

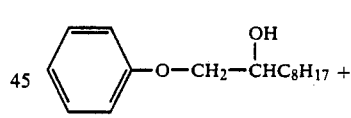

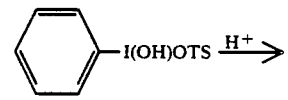

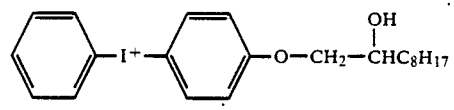

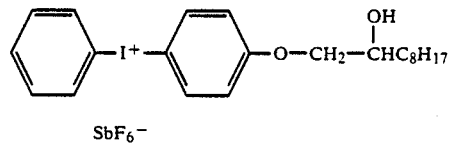

Combined together were 5.0g (0.02 mol) 1-phenoxy-2-hydroxydecane, 7.84 g (0.02 mol) [hydroxy(tosyloxy)iodo]benzene, 50 mL methylene chloride and 2 mL glacial acetic acid. The reaction mixture was heated at reflux (40° C.) for two hours to give a yellow, nearly transparent solution. The methylene chloride was removed on a rotary evaporator and then 100 mL acetone was added. Next, there were added to the solution 5.18 g (0.02 mol) NaSbF$_6$ and the reaction mixture was stirred. Immediate formation of a white precipitate of sodium p-toluenesulfonate was formed which was removed by suction filtration. The acetone was then stripped off under vacuum leaving a pale yellow oil of the iodonium salt photoinitiator, [4-(2-hydroxy-1-decyloxy)phenyl] phenyliodonium hexafluoroantimonate. On standing, the oil tended to slowly crystallize.

A 1% solution of the above photoinitiator dissolved in 4-vinylcyclohexene dioxide and spread as a 3 mil film on glass, cured to a hard, transparent crosslinked coating within 5 seconds when exposed to UV light from a GE H3T7 medium pressure mercury arc lamp ballasted at 200 W.

EXAMPLE 2

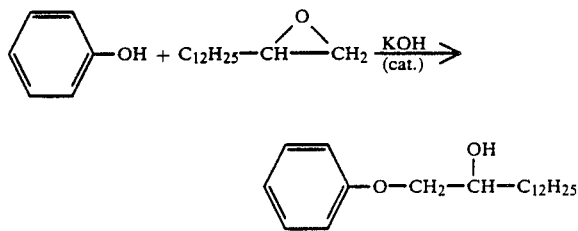

The same procedure described above was used to prepare 1-phenoxy-2-hydroxytetradecane. Combined together were 42.4g (0.2 mol) 1,2-epoxytetradecane, 28.2g (0.3 mol) phenol and 0.5 g KOH. The reaction mixture was heated at 120-130° C. for one hour, then cooled, poured into a separatory funnel, diluted with methylene chloride and washed twice with 1 N KOH solution to remove the phenol. Saturated brine was added to break the emulsion. Finally, the reaction mixture was washed with distilled water and the organic layer dried over magnesium sulfate. The solvent was removed on a rotary evaporator yielding a pale yellow oil. On cooling the oil crystallized to give a waxy solid. The yield was 52.4 g (86% theory). M.W.=306, $C_{20}H_{34}O_2$. The crude product may be recrystallized from hot n-hexane (m.p. 80-81° C.).

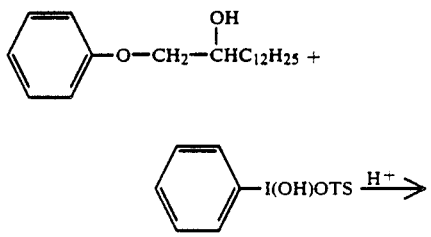

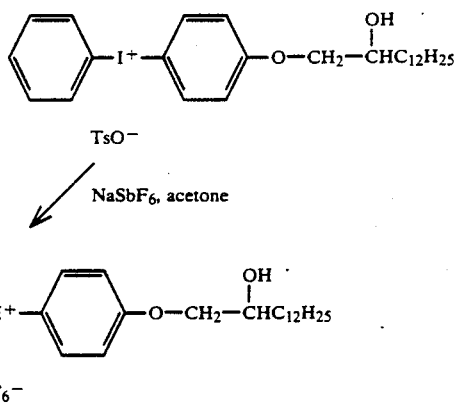

As described in example 1, there were combined together 7.84 g (0.02 mol) [hydroxy(tosyloxy)iodo]benzene, 6.12 g (0.02 mol) 1-phenoxy-2-hydroxytetradecane, 40 mL methylene chloride and 5 mL glacial acetic acid. The reaction mixture was heated under reflux until the [hydroxy(tosyloxy)iodo]benzene had dissolved (3 hours). The methylene chloride was removed using a rotary evaporator and the pale yellow oil redissolved in 75 mL acetone. There were added 5.16 g (0.02 mol) NaSbF$_6$ and the reaction mixture was stirred. Immediate separation of sodium p-toluenesulfonate took place and the reaction mixture was filtered using suction filtration. The acetone was removed by evaporation leaving a yellow oil. Distilled water was added and the oil washed several times. On standing overnight, the oil crystallized and the product was briefly dried and weighed. There were obtained, in two separate trials, 12.7 g (85% yield) and 12.9 g (86.5%) of the desired iodonium salt. M.W.=746, $C_{26}H_{39}O_2ISbF_6$. The salt could be purified and crystallized by washing it with hexane or toluene. On drying, the compound had a melting point of 93-95° C. The salt may be readily recrystallized from hot toluene.

The above iodonium salt was an excellent photoinitiator for cationic polymerization. Using the irradiation conditions described in the previous example, 4-vinylcyclohexene dioxide was tackfree in 5 seconds, polybutadiene oxide in 10 seconds, and diethylene glycol divinyl ether in one second.

A 1% solution of the above iodonium salt initiator was prepared in 4-vinylcyclohexene dioxide. To this solution there were added 0.1% copper naphthenate (12% in mineral oil) and 1% by weight stannous octoate. On mixing, the green copper color was discharged and polymerization took place immediately and exothermically. This is an example of the use of a redox catalyzed cure of an epoxy resin using the hydroxy-substituted iodonium salts of the instant invention.

The same test as shown above was repeated omitting the tin reducing agent. On heating the catalyzed epoxy mixture to 100° C., rapid exothermic polymerization took place. This example demonstrates the use of the hydroxy-substituted iodonium salts of this invention in heat-activated cures of epoxy resins.

The above example was repeated again, replacing NaSbF$_6$ with 3.68 g KPF$_6$. There were obtained, after washing with water and hexane, 7.34 g (56.4% yield) of the desired iodonium hexafluorophosphate salt. A 1% solution of the salt in 4-vinylcyclohexene dioxide gave a tackfree film after 15 seconds irradiation as described above.

EXAMPLE 3

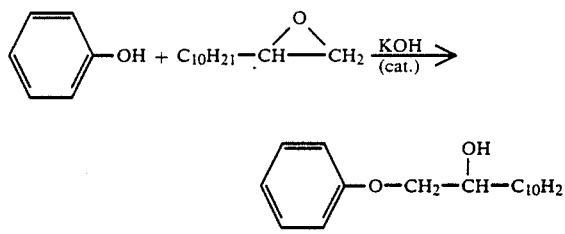

As in the above two experiments, there were reacted together 36.8g (0.2 mol) 1,2-epoxydodecane, 28.2 g (0.3 mol) phenol and 0.5g KOH. Reaction was continued for two hours at 130° C. The product, 1-phenoxy-2-hydroxydodecane was dissolved in ether, extracted with KOH, washed with water and isolated by removal of the solvent. Purification was achieved by recrystallization from n-hexane. The product, (23.82 g) 1-phenoxy-2-hydroxydodecane, had a melting point of 70-72° C.

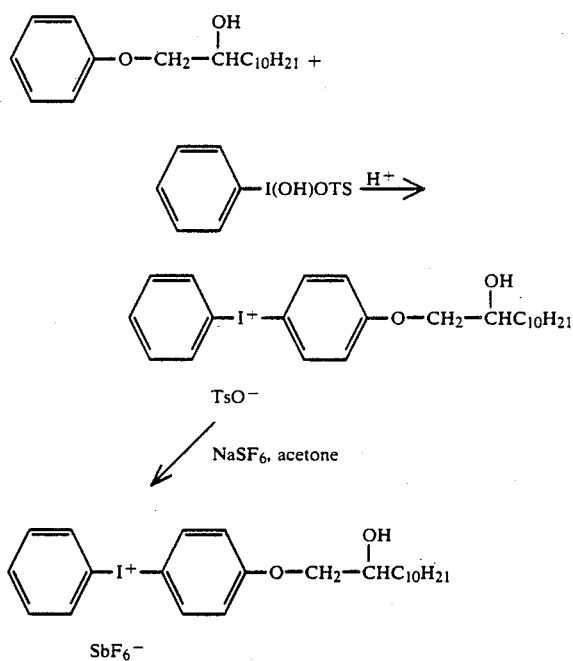

A mixture of 5.96 g (0.02 mol) 1-phenoxy-2-hydroxydodecane, 7.84 g [hydroxy(tosyloxy)iodo]benzene, 40 mL methylene chloride and 10 mL glacial acetic acid were reacted together at reflux for one hour. A yellow solution was obtained which was treated as in the previous example. After addition of 40 mL acetone and 5.18 g $NaSbF_6$, the reaction mixture was filtered and the filtrate placed on a rotary evaporator. On addition of distilled water, followed by washing the oil several times, the iodonium salt product crystallized. The product was filtered and dried to give 15.5 g of the desired iodonium salt. The compound was recrystallized from toluene (m.p.91.9° C.). Ultraviolet irradiation of a one mil film containing the biscycloaliphatic epoxide, 3,4-epoxycyclohexylmethyl-3′,4′-epoxycyclohexane carboxylate, and 2% of the above photoinitiator gave a crosslinked tackfree film in 15 seconds.

EXAMPLE 4

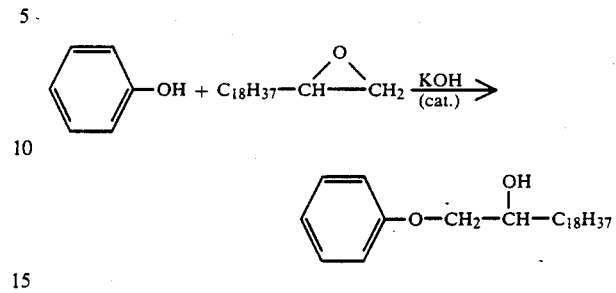

Combined and reacted at 130° C. were 29.6 g (0.1 mol) 1,2-epoxycosane, 15g (0.16 mol) phenol and 0.5 g KOH as a catalyst. After one and one-half hours, the reaction mixture was cooled, dissolved in hot n-hexane and allowed to crystallize. The product was isolated by suction filtration and allowed to air dry. The product had a melting point of 83-85° C.

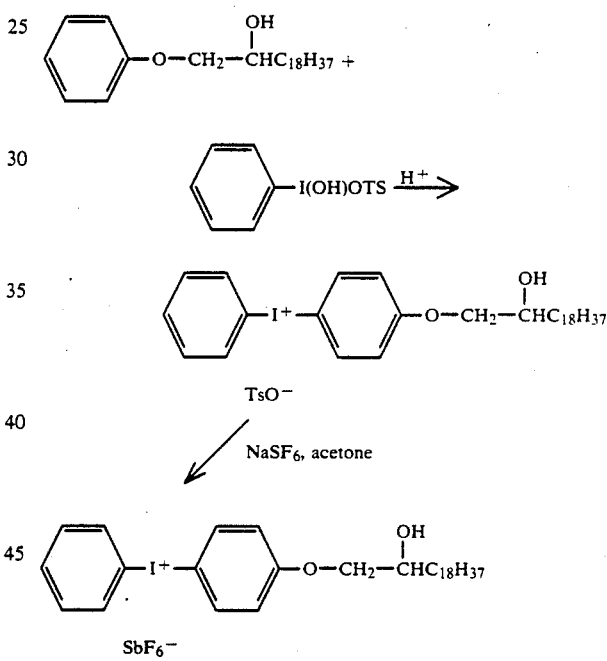

To 7.80 g.(0.02 mol) of 1-phenoxy-2-hydroxycosane there were added 7.84 g (0.02 mol) [hydroxy(tosyloxy)iodo]benzene, 35 mL methylene chloride and 10 mL glacial acetic acid. The reaction mixture was heated to reflux for one and one-half hours. After removal of the methylene chloride under vacuum, the yellow oil was diluted with 40 mL acetone, and 5.18 g (0.02 mol) $NaSbF_6$ was added. The reaction mixture was further diluted with acetone and then filtered to remove the sodium p-toluensulfonate. The acetone was evaporated from the reaction mixture. On addition of distilled water, the product crystallized to give a pale yellow crystalline salt. A 1% solution of this crude salt in 4-vinylcyclohexene dioxide gave a tackfree film in 5 seconds irradiation under the conditions described in Example 1. The photoinitiator was recrystallized from toluene to give the pure iodonium salt in the amount of 13.04 g (78.6% yield).

What is claimed is:

1. A method for quantitative synthesis of broadly soluble diaryliodonium photo- and thermo-active polymerization initiator salts of the formula,

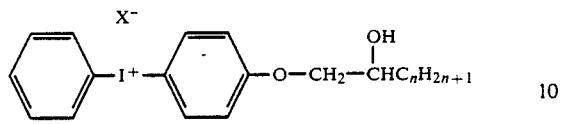

in which the values of n are integers from 0 to 25 and X⁻ includes complex metal halide anions such as $BF_4^-$, $PF_6^-$, $AsF_6^-$, $SbF_6^-$, and anions of strong protonic acids such as $ClO_4^-$, $CF_3SO_3^-$, $FSO_3^-$, $CH_3SO_3^-$, and $C_4F_9SO_3^-$, comprising reacting a compound of the formula,

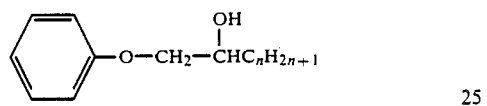

with [hydroxy(tosyloxy)]iodobenzene in the presence an organic solvent and a reagent providing an anion of a complex metal halide or a strong protonic acid, as aforesaid.

2. A method for producing up to excellent yields of highly soluble diaryliodonium photo-and thermo-initiator salts in which aryl groups are substituted with long chain alkoxy groups which possess 2-position hydroxyl moieties, said method comprising reacting a monoaryloxy-2-hydroxyalkane with [hydroxy(tosyloxy)iodo]benzene in the presence of a suitable solvent and further providing an anion source from a complex metal halide or a strong protonic acid.

3. The method of claim 2 wherein said salts with 2-position hyroxyl moieties comprise molecules of the formulae:

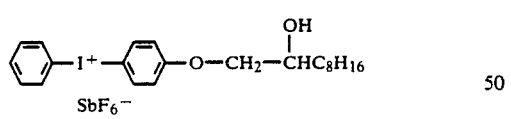

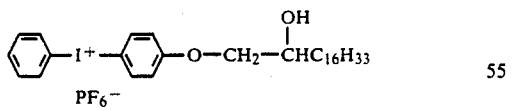

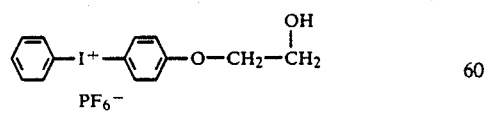

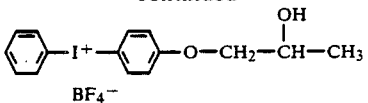

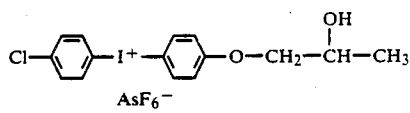

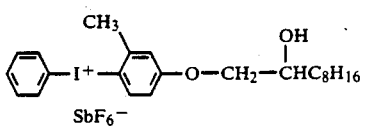

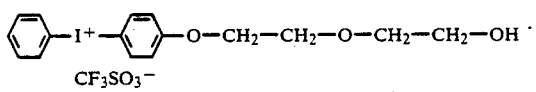

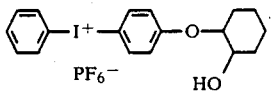

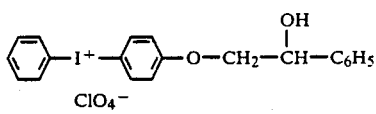

4. The method according to claim 2 wherein the providing step comprises including an anion from the groups:

$BF_4^-$, (a)
$PF_6^-$,
$AsF_6^-$,
$SbF_6^-$, or $ClO_4^-$, (b)
$CF_3SO_3^-$,
$FSO_3^-$,
$CH_3SO_3^-$,
$C_4F_9SO_3^-$, where (a) are complex metal halide anions and (b) are anions of strong protonic acids.

5. A highly soluble photo-and thermo-active diaryliodonium salt initiator of the formula:

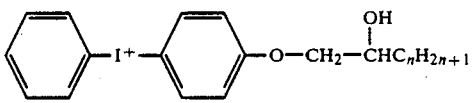

where n represents an integer from 0 to 25 and X⁻ includes anions of complex metal halides or strong protonic acids.

6. The initiator of claim 5 including an anion of the following groups: $BF_4^-$, $PF_6^-$, $AsF_6^-$, $SbF_6^-$, $ClO_4^-$, $CF_3SO_3^-$, $FSO_3^-$, $CH_3SO_3^-$ and $C_4F_9SO_3^-$.

* * * * *